United States Patent [19]

Edwards et al.

[11] Patent Number: 5,394,988
[45] Date of Patent: Mar. 7, 1995

[54] PALLET FOR RECEIVING AND TRANSPORTING OPHTHALMIC LENS CONTAINERS

[75] Inventors: Russell J. Edwards; James A. Ebel, both of Jacksonville, Fla.; Borge P. Gundersen, Tikob; Thomas C. Ravn, Helsingor, both of Denmark

[73] Assignee: Johnson & Johnson Vision Products, Inc., Jacksonville, Fla.

[21] Appl. No.: 170,436

[22] Filed: Dec. 20, 1993

Related U.S. Application Data

[63] Continuation of Ser. No. 994,242, Dec. 21, 1992, abandoned.

[51] Int. Cl.6 .............................................. A45C 11/04
[52] U.S. Cl. .................................... 206/5.1; 206/562; 206/563
[58] Field of Search ................. 206/5.1, 477, 483, 486, 206/490, 562, 563, 0.83, 0.84, 538, 539; 134/901

[56] References Cited

U.S. PATENT DOCUMENTS

| | | | |
|---|---|---|---|
| 2,492,081 | 12/1949 | Williams | 206/562 |
| 3,649,464 | 3/1972 | Freeman | 206/562 |
| 4,269,307 | 5/1981 | LaHaye | 206/5.1 |
| 4,294,931 | 10/1981 | Levin et al. | 206/562 |
| 4,384,649 | 5/2983 | Brodsky | 206/538 |
| 4,565,348 | 1/1986 | Larsen . | |
| 4,640,489 | 2/1987 | Larsen . | |
| 4,784,258 | 11/1988 | Figari | 206/5.1 |
| 4,928,815 | 5/1990 | Paul | 206/5.1 |
| 4,998,623 | 3/1991 | Doull | 206/539 |
| 5,080,839 | 1/1992 | Kindt-Larsen | 206/5.1 |
| 5,143,660 | 9/1992 | Hamilton et al. . | |
| 5,904,609 | 3/1992 | Kindt-Larsen | 425/445 |

FOREIGN PATENT DOCUMENTS

| | | |
|---|---|---|
| 2057832 | 6/1992 | Canada . |
| 82103214 | 11/1982 | European Pat. Off. . |
| 3432002C2 | 3/1982 | Germany . |
| 2171812B | 3/1985 | United Kingdom . |

*Primary Examiner*—David T. Fidei

[57] ABSTRACT

An ophthalmic lens pallet having wells for receiving one or more lens containers at the receiving point achieves the requisite uniformity of motion in the direction of motion, and stability when transporting the lens in the orthogonal, non-translating directions by restraining the pallet between rails. A spring-loaded roller ball located on the side walls of the pallet body cooperate with guide rails on the conveyor to compress the spring-loaded roller ball when the pallet is between the guide rails. Blind holes on the pallet engage a drive which transports the pallet from the lens receiving point to an inspection station then to a lens disposition mechanism. The pallet wells comprise holes that pass through the pallet. These holes along with the rail and transport system make possible an arrangement of a lamp and camera for capturing an image of a lens.

11 Claims, 1 Drawing Sheet

PALLET FOR RECEIVING AND TRANSPORTING OPHTHALMIC LENS CONTAINERS

This is a continuation of application Ser. No. 07/994,242, filed Dec. 21, 1992, now abandoned.

BACKGROUND OF THE INVENTION

Previous inspection of ophthalmic lenses, especially molded, hydrophilic contact lenses, employed human inspection utilizing trays having a rectangular array of wells in which the lenses were submerged in saline solution.

In this system, a tray containing lenses and saline is transferred to an inspection station attended by a human operator. When the tray is placed in the inspection station, a viewing assembly is positioned above a first well. The lens in the well is illuminated from below and an image is transferred by the viewing apparatus and projected upon a screen at the inspector's eye-level.

After looking for the appropriate lens characteristics and deviations from accepted standards, the human inspector makes a decision as to whether the lens is acceptable. The inspector often finds it is useful to move or displace the lens slightly relative to the tray well in which it is contained, or to otherwise disturb the saline solution, in order to distinguish between foreign particles in the saline and imperfections in the tray well from characteristics or defects on the lens.

The inspector enters his decision by pushing the appropriate electrical switch to indicate that the lens is either acceptable or to be rejected. The viewing mechanism then indexes over to the next well in the tray where the inspection procedure is repeated. As can be appreciated, certain time constraints must be placed upon the inspector such that if a decision is not made within a predetermined amount of time, the lens is automatically considered defective, and the viewing apparatus indexes to the next well. Likewise, lenses that may otherwise be acceptable but are accompanied by extraneous pieces of foreign material or if two lenses are found in the same well, the situation is considered unacceptable and the contents of the well rejected.

Upon the completion of the inspection of an entire tray of lenses, the inspector activates another electrical switch to initiate disposition of the lenses of the tray just inspected. A disposal unit visits each well of the tray where an unacceptable lens was indicated to suction out and dispose of those lenses. The tray is then transferred along for the packaging of the acceptable lenses.

As can be appreciated by one skilled in the art, although the inspectors are highly trained and are given objective criteria by which to judge the quality and ultimate acceptability of the lenses, human inspection leaves much to be desired. Human inspectors lack inspector-to-inspector uniformity, and repeatability by a single inspector may be lacking based on the inspector's mental condition and accumulated fatigue.

An automated inspection system can be implemented where an image of the lens to be inspected is captured using a strobe lamp and a camera and the image then digitized and processed by a computer to make a determination whether the lens is acceptable.

There are with such a system, however, a number of requirements particular to this type of automated inspections that are not found when using human inspection.

Because of the limited field-of-view of a camera system, and the desire to utilize the field to the maximum extent, it is important that the .lens be centered in the field while it is being carried so that lenses are found in a repeatable position from one lens to the next.

Due to the manner in which an image is captured by the camera, a second requirement is that the image be as clear as possible and not blurred by external vibrations, either of the lens or the saline in which it is placed. For this reason, it is necessary that the transport system carrying the container in which the lens is found travels as uniformly as possible in the direction in which the lens is traveling and is stationary in the two orthogonal directions.

Both of these requirements must be met while permitting the lamp and camera to be positioned to allow the camera to capture a high quality image of the lens. It is preferable that the above objectives be achieved while the lamp and camera are on opposite sides of the lens allowing the light to pass through the lens, an image to be captured by the camera then digitized. These requirements mandate that the mechanism for holding and moving the lenses be located substantially to the sides of the lens travel path in order not to obstruct the light from the lamp from which the image is captured.

The above requirement of capturing a clear, well-centered image of the lens further dictates that there be a precise triggering mechanism associated with each lens to activate a sensor to illuminate the strobe lamp.

A further object of the present invention is provide a receptacle for receiving one or more contact lens containers that can then be transported by a conveyor to an inspection station comprising the lamp and camera.

SUMMARY OF THE INVENTION

The above objects are achieved by a lens pallet having wells for receiving one or more lens containers at the receiving point.

The pallet of the present invention achieves the requisite uniformity of motion needed in the direction of motion and stability when transporting the lens in the orthogonal, non-translating directions by the use of guide rails. The pallets are restrained between the rails, except in the direction of travel, by mechanical bias means such as a spring-loaded roller ball located on the side walls of the pallet body which cooperate with guide rails on the conveyor positioned to compress the mechanical bias means when the pallet is between the guide rails. Engagement means on the pallet are also provided for engaging a drive means which transports the pallet from the lens receiving point to an inspection station then to a lens disposition mechanism.

The pallet wells for receiving the containers comprise holes that pass through the pallet. These holes along with the above-described guide and transport system make possible an arrangement of the lamp and camera for capturing an image of a lens that maximizes utilization of the field-of-view of the camera and minimizes blurring.

A computer implemented algorithm then processes the digitized image according to rules set forth in a computer program to determine the acceptability of and disposition of the lenses.

BRIEF DESCRIPTION OF THE DRAWINGS

The Figure is a an isometric view of an apparatus constructed according to the present invention.

DESCRIPTION OF THE PREFERRED EMBODIMENT

Figure 1:
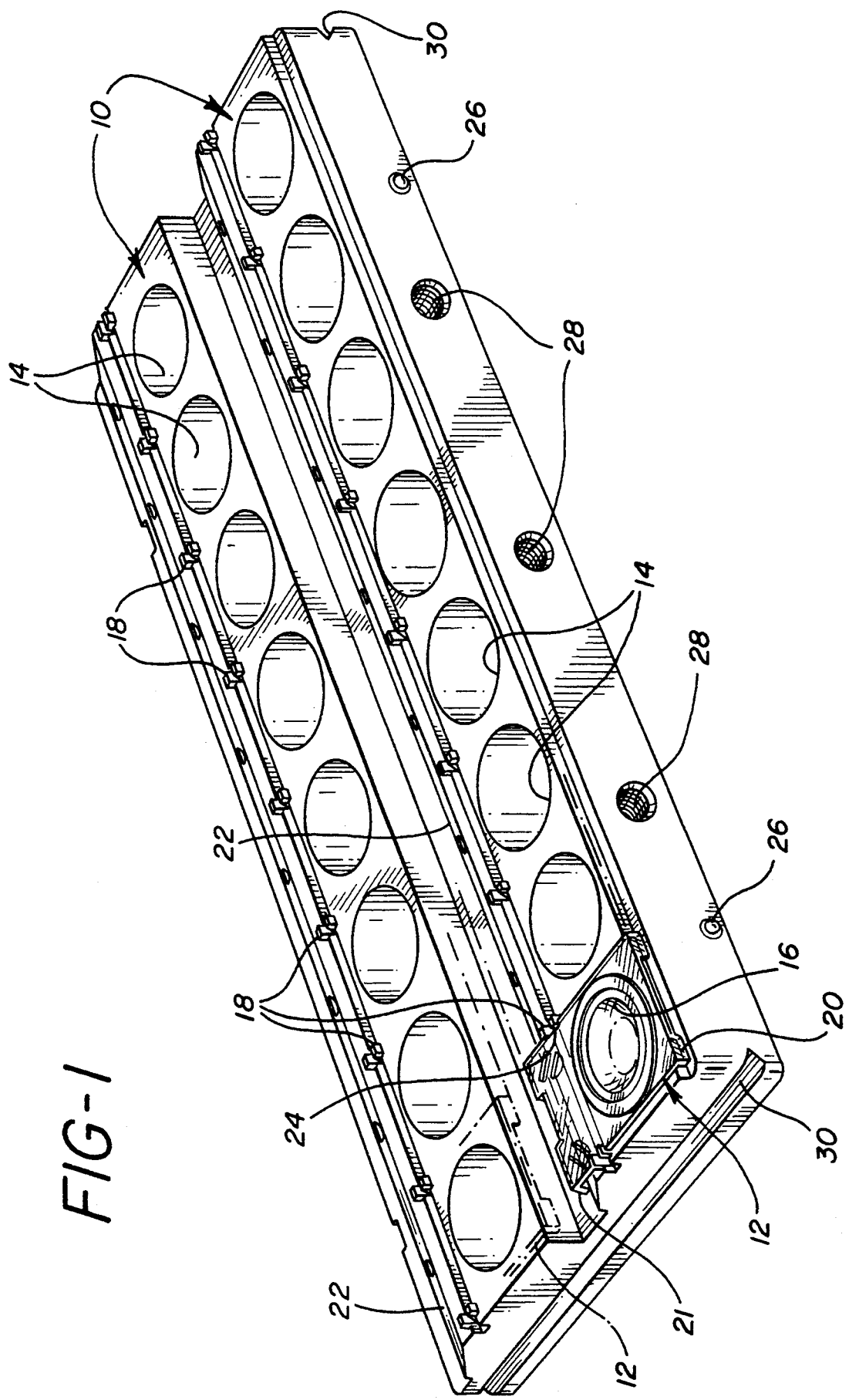

Referring to the Figure, there is shown a pallet constructed according to the present invention. The pallet comprises wells 10 that are constructed to receive a lens container such as package 12.

Comprising a portion of the well is hole 14 which passes through the pallet from the top to the bottom. The bowl 16 of package 12 fits within the hole 14. In the bowl 16 of package 12 rests a hydrated contact lens (not shown).

A more detailed description of the preferred embodiment of the lens package is given in copending U.S. application Ser. No. 995,607 filed Dec. 21, 1992 for Ophthalmic Lens Package.

In addition, the pallet contains locating means such as projections 18 which interlock with a mating locating means such as the notches on container 12.

These locating means of container 12 serve to interlock the container onto the pallet such that the container is restrained in at least two dimensions on the pallet.

In addition, the preferred embodiment of the present invention contains groove or notch 22 which serves to accommodate a portion of the package projecting beyond the top plane of the bowl and the downward projecting side portion 21 opposite the other side portion 20.

In addition, each well contains associated therewith a triggering means such as the notch inner edge 24 of container 12. The triggering means, such as notch inner edge 24, is capable of activating a sensor which is responsive to the reflectance of light from the package surface. The notch inner edge or any other surface used for triggering purposes must be constructed within tolerances sufficient to keep the lens within the field-of view of the inspection camera. This sensor is of the type such as the Keyence FS2-65 Amplifier and FU-65 Fiber Optic Unit from Keyence, Inc. of Fairlawn, N.J.

The method of capturing an lens image with a camera and determining whether a lens is acceptable once an image is captured by the camera and reduced to digital data is described in copending U.S. application Ser. No. 993,756 filed Dec. 21, 1992 for Ophthalmic Lens Inspection Method and Apparatus.

In this embodiment, the triggering means is a portion of the container; it may, however, be constructed as part of the pallet depending upon the needs of the designer. In such a particular embodiment, the triggering means may be a portion of the pallet highly reflective, and substantially different from the reflectance of the pallet in range of the sensor.

In either case, the sensor is activated by emission of light from a lamp which is then detected by a photodiode reflected from notch inner edge 24 (or alternately by the highly reflective pallet surface) when in the proper position to transmit the light back to the photodiode.

A more detailed description of the preferred embodiment of the illuminating system is given in copending U.S. application Ser. No. 994,388 filed Dec. 21, 1992 for Illumination System for Ophthalmic Lens Inspection.

In addition to the triggering means each associated with one of the pallet wells, there may be provided additional triggering means. Additional triggering means may be utilized for indicating the presence of the entire pallet. In this instance the edge of the pallet is used by simply interrupting a light beam directed through the path of the pallet, but may be a separate triggering means such as that for the individual wells. The additional entire pallet triggering means is used to indicate the initiation of inspection on a new pallet, thereby maintaining manufacturing accountability if an interruption occurs during the inspection procedure. By including a means for indicating the presence of a new pallet, strict accountability can be maintained of lens production, inspection results and pallet inventory. The light beam and detection is performed by a sensor such as the FS2-65 Amplifier with a FU-35f Fiber Unit and F-3H attachment from Keyence of Fair Lawn, N.J.

One side of the pallet contains mechanical bias means such as spring-loaded roller ball 26 which is a sphere projecting beyond the plane ,of the pallet and free to rotate. The projecting sphere can be returned into a hole in the side of the pallet by compression of the spring providing the outward mechanical bias.

In order to move the pallets in the direction of travel uniformly and consistently and to reduce vibration and other extraneous motion in the non-travel directions, the mechanical bias such as the spring-loaded roller ball 26 located on the side walls of the pallet body, cooperate with guide rails on the conveyor and are positioned to compress the mechanical bias means when the pallet is placed between conveyor guide rails.

To transport the pallets, the conveyor system further comprises drive means which engage engagement means such as blind holes 28 located in the sides of the pallets. As the drive means move along rails, the pallets are smoothly and uniformly transported between the guide rails.

A more detailed description of the preferred embodiment of the lens transport system is given in copending U.S. application Ser. No. 994,249 filed Dec. 21, 1992 for Ophthalmic Lens Inspection System and Method.

The pallet is coated with a durable coating with high lubricity of the type such as Tufram C22 or Magnaplate HCR (General Magnaplate Corporation, Linden, N.J.). This coating also serves to inhibit corrosion in the presence of processing liquids. The guide rails are of a compatible material to ensure flatness and that no particles are generated.

The pallet of the preferred embodiment also contains gripping areas 30 which allow a pick and place robot with a gripper (not shown) to securely hold the pallet when removing or placing a pallet into the inspection system. The gripping areas in the present embodiment comprise grooved slots 30, but in the alternative consist of projections, holes or ledges.

We claim:

1. An apparatus for receiving, transporting and inspecting ophthalmic lenses, the apparatus comprising:
    a pallet body having a top surface, a bottom surface, and wells for receiving one or more ophthalmic lens containers, the wells comprising holes passing through the pallet from the bottom surface to the top surface thereof,
    an ophthalmic lens container removably held in one of said wells,
    a locating means for restraining the container in at least two dimensions on the pallet,
    a pallet engagement means for engaging a drive means for transporting the pallet, and
    a triggering means responsive to the presence of an ophthalmic lens container and triggering lens inspection.

2. The apparatus of claim 1 wherein the triggering means comprises one triggering means for each of the wells.

3. The apparatus of claim 1 wherein wells are located in parallel rows.

4. The apparatus of claim 1 wherein the triggering means comprises a single pallet presence indicator.

5. The apparatus of claim 2 wherein the triggering means is the container edge.

6. The apparatus of claim 2 wherein the triggering means is a portion of the pallet having a reflectance different from the remainder of the pallet within range of the sensor sufficient to activate the sensor.

7. The apparatus of claim 2 wherein the a projection breaks the plane of the surface of the pallet body and each serves as locating means by interlocking with mating locating means on a lens container, the locating means and the mating locating means restraining the container in at least one dimension on the pallet when interlocked.

8. The apparatus of claim 1 wherein the mechanical bias means located on at least one of the side walls of the pallet body is a spring-loaded roller ball.

9. The apparatus of claim 1 wherein the pallet body further comprises gripping areas that secure with a robot gripper.

10. The apparatus of claim 1 further comprising a mechanical bias means located on at least one of the side walls of the pallet body, said side walls substantially perpendicular to the top and bottom pallet surfaces.

11. The apparatus of claim 1 wherein the locating means for restraining the container comprises mating locating means on the lens container interlocking with the locating means on the pallet body.

* * * * *